United States Patent
Koyanagi (10) Patent No.: US 6,516,047 B2
(45) Date of Patent: Feb. 4, 2003

(54) X-RAY DIFFRACTION APPARATUS AND METHOD

(75) Inventor: Kazuo Koyanagi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/901,821

(22) Filed: Jul. 9, 2001

(65) Prior Publication Data

US 2002/0003857 A1 Jan. 10, 2002

(30) Foreign Application Priority Data

Jul. 10, 2000 (JP) ........................................ 2000-208222

(51) Int. Cl.⁷ ............................................... G01N 23/20
(52) U.S. Cl. ............................ 378/70; 378/81; 378/150
(58) Field of Search .............................. 378/70, 71, 81, 378/82, 150

(56) References Cited

U.S. PATENT DOCUMENTS 5,748,509 A * 5/1998 Fewster ....................... 364/578
6,310,935 B1 * 10/2001 Kuwabara .................... 378/49
6,310,937 B1 * 10/2001 Van Den Hoogenhof ..... 378/71

FOREIGN PATENT DOCUMENTS

JP 402296138 * 12/1990 ................... 378/70

* cited by examiner

Primary Examiner—Drew A. Dunn
Assistant Examiner—Elizabeth Gemmell
(74) Attorney, Agent, or Firm—Beyer Weaver & Thomas LLP (57) ABSTRACT

An x-ray diffraction apparatus for qualitatively analyzing a sample uses a fixed or variable divergence slit to irradiate a portion of its surface and intensity data are collected at different angles of diffraction. When measured data thus obtained are compared with reference data for the qualitative analysis, the measured data, the reference data or both of these data are corrected in part according to whether the reference data were taken by measurements using a fixed or variable divergence slit such that the comparison can be carried out on the same intensity level and the qualitative analysis can be carried out more accurately.

18 Claims, 6 Drawing Sheets

X-RAY DIFFRACTION APPARATUS AND METHOD

BACKGROUND OF THE INVENTION

This invention relates to x-ray diffraction apparatus and method and more particularly to an x-ray diffraction apparatus provided with means for correcting data in qualitative analyses and a method of x-ray diffraction analysis by making use of such an apparatus.

When a beam of x-rays is made incident on a crystalline surface, the beams reflected by the latticed crystalline surface interfere and the intensity of the diffracted beams in directions satisfying Bragg's formula is increased while the beams diffracted at other angles are cancelled and are not observed. The x-ray diffraction method makes use of this phenomenon and carries out qualitative analysis of a sample material from the relative intensity of diffracted x-ray beams corresponding to the lattice surface spacing which is characteristic of the material. X-ray diffraction apparatus using a goniometer have been used for measuring the angle between an x-ray beam incident on a sample and a beam diffracted thereby and its intensity.

Qualitative analyses by x-ray diffraction are carried out by comparing the intensity pattern of diffracted x-rays obtained by a measurement on a sample with reference patterns of diffracted x-rays obtained by measurements on standard (or reference) materials. Such reference patterns of standard materials are usually used in a preliminarily prepared form such as a database.

Figure 7A:
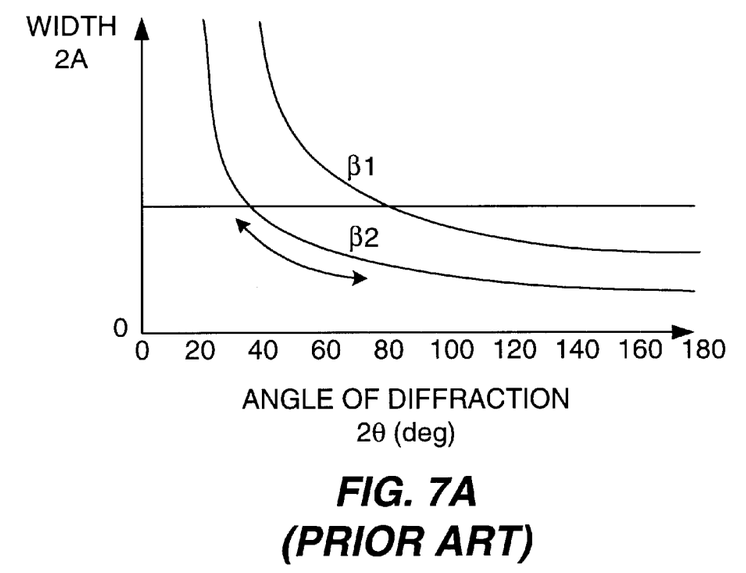
FIGS. 7A and 7B are graphs showing the relationship between angle of diffraction and the width of irradiated area.
Figure 7B:
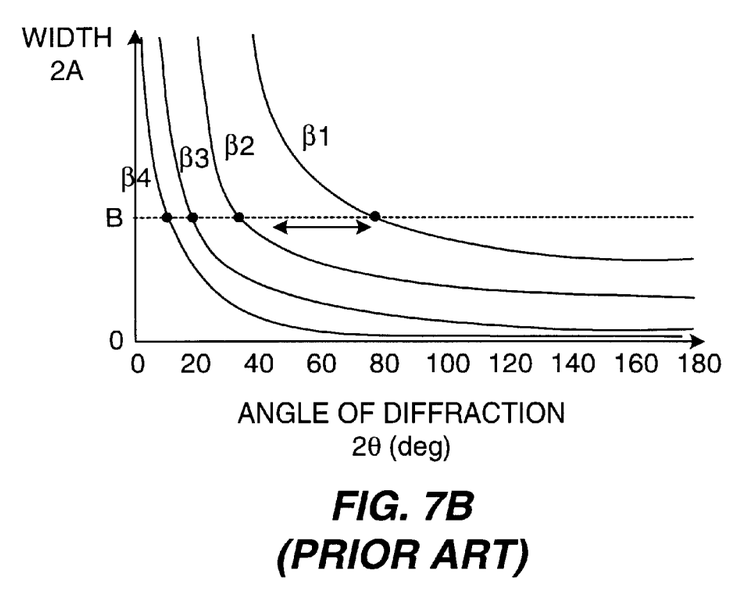

Both a slit with a fixed aperture ("a fixed slit") and a slit with a variable aperture ("a variable slit") are used to serve as a divergence slit for determining the width of the x-rays to be made incident on a sample surface. If a fixed slit is used, the width of the irradiated area on the sample ("the irradiated width") varies as the angle of diffraction is changed. If a variable slit is used, on the other hand, the angle of the opening ("the divergence angle" or "the angle of divergence") is caused to change with the diffraction angle such that the irradiated width will remain constant. FIG. 7A is a graph which shows the relationship between the angle of diffraction (2θ) and the irradiated width (2A) when a fixed slit is used, and FIG. 7B is a graph which shows the relationship between the angle of diffraction (2θ) and the irradiated width (2A) when a variable slit is used to keep the irradiated width constant (shown by a broken line).

If a fixed slit is used, the angle of divergence β is a fixed angle corresponding to the selected slit, independent of the angle of diffraction, and the irradiated width changes according to the angle of diffraction. If the broken line in FIG. 7A is taken as representing an effective width of a sample, it can be understood that only a portion of the effective width is irradiated at a large angle of diffraction but that the irradiated width becomes greater than the effective width at a small angle of diffraction, a portion of the incident x-ray beam becoming wasted. If a variable slit is used, on the other hand, the angle of divergence β is controlled as the angle of diffraction is varied such that the irradiated width will stay constant independent of the angle of diffraction (as shown by the broken line in FIG. 7B).

Qualitative analyses are carried out by comparing measured intensity data of diffracted x-rays with reference intensity data and based upon the peak positions and the ratios among the peak intensities. Ordinarily, the intensity data of diffracted x-rays of standard materials are obtained by using a fixed divergence slit. For obtaining intensity data of diffracted x-rays from a target sample, however, use may be made of a variable slit as well as a fixed slit. When measured data obtained by using a variable slit are compared with reference data obtained by using a fixed slit, or when measured data obtained by using a fixed slit are compared with reference data obtained by using a variable slit, the comparison of intensity ratio of diffracted x-rays cannot be made under the same conditions because the irradiated width is constant with a variable slit but varies according to the angle of diffraction with a fixed slit. Even if reference data and measured data are each obtained by using a fixed slit, furthermore, the width of the irradiated area may be different if the fixed slits have different angles of divergence. In such a situation, the intensity of the diffracted x-rays will become different even at a same angle of diffraction and the intensity ratio of diffracted x-rays cannot be compared under the same conditions.

In summary, conventional x-ray diffraction apparatus could not carry out accurate qualitative analyses because of the error which will result between measured and reference intensity data when the measured and reference data are obtained under different conditions and, in particular, if different divergence slits are used.

SUMMARY OF THE INVENTION

It is therefore an object of this invention to provide an x-ray diffraction apparatus and method capable of comparing measured data and reference data accurately for an accurate qualitative analysis even where the measured and reference data are obtained under different conditions and, in particular, by using different divergence slits.

When measured and reference data are compared in a qualitative analysis by x-ray diffraction according to this invention, the measured data and/or the reference data are corrected so as to make the conditions of measurement of these data equal such that the ratio of measured and reference intensity data can be compared accurately and the qualitative analysis can be carried out accurately. The invention is particularly addressed to the correction of the errors in the intensity ratios caused by using different divergence slits.

An x-ray diffraction apparatus embodying this invention may be characterized as including a data correcting means for making corrections on the measured and/or reference intensity data and thereby correcting the intensity ratio according to the width of the divergence slit. The divergence slit is a slit for determining the divergence angle of the x-rays and hence the area on the sample irradiated by the x-rays and may be a fixed slit or a variable slit.

Aforementioned measured and reference data are intensity data of diffracted x-rays obtained respectively from a target sample and reference samples. The difference in the choice of whether to use a fixed slit or a variable slit for making the width of the irradiated area constant appears only as the difference in the width of the irradiated area. The data correcting means is for correcting the difference between the intensity levels of diffracted x-rays caused by the difference in the width of irradiated area, depending on the kind of divergence slit. Either or both of the measured and reference data are corrected by using a single selected width as a standard width. By thus making a correction or corrections, it becomes possible to compare the intensities of diffracted x-rays of measured and standard data under the same conditions. The data correcting means serves to use the ratio between the width of the area on a sample irradiated by x-rays when a fixed slit is used and that of a fixed irradiated area when a variable slit is used and to multiply either the measured data or the reference data with this ratio to thereby match the intensity of either to the intensity level of the other. It may also use a selected standard width different from either of the widths corresponding to the measured and reference data and multiply correspondingly the ratios between these widths of the irradiated areas and this selected standard width to the measured and reference data so as to match their intensity levels at this selected standard width.

DETAILED DESCRIPTION OF THE INVENTION

Figure 1:
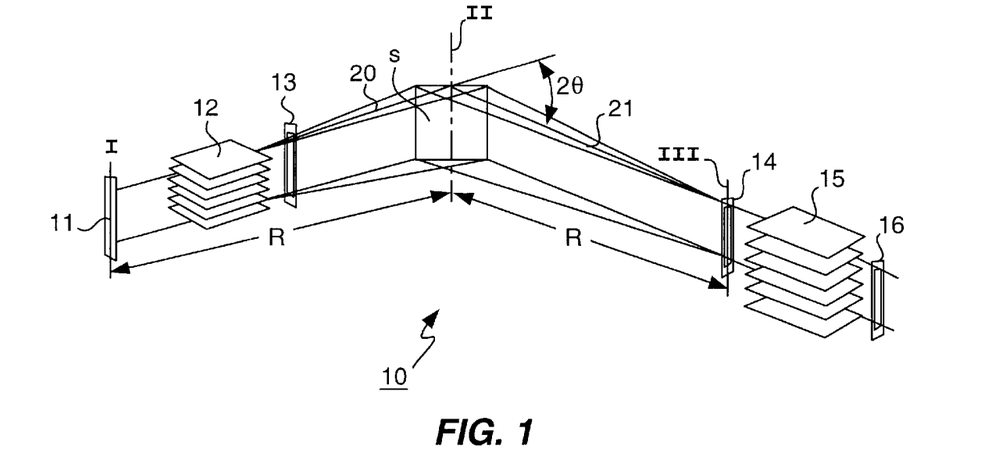
FIG. 1 is a schematic perspective view of an optical system of an x-ray diffraction apparatus using a goniometer.
Figure 2:
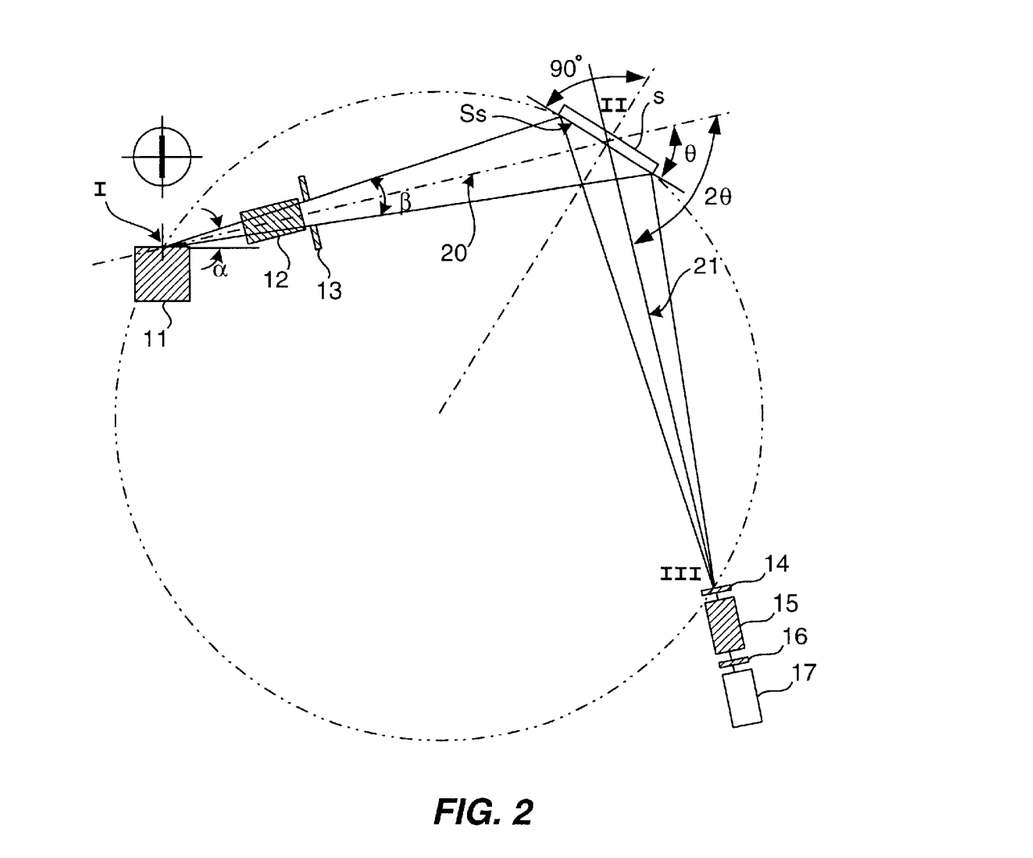
FIG. 2 is a schematic drawing of the optical system of FIG. 1 for showing its geometrical relationship.

The invention is described next by way of an example. FIGS. 1 and 2 are schematic drawings for showing approximately an example of the structure of an x-ray diffraction apparatus embodying this invention with an optical system 10 including a goniometer which comprises an x-ray source 11, first Soller slits 12, a divergence slit 13, a light receiving slit 14, second Soller slits 15, a so-called scatter slit 16 (not for scattering the x-rays but for preventing scattered x-rays in the environment from entering into the detector) and a counter tube 17. A sample (indicated by letter S) is placed such that a center point on its surface Ss is at a same distance (the radius R of the goniometer) both from the x-ray source 11 and the light receiving slit 14 and that the sample surface Ss is tangent to the circumference of the circle determined by this center point, the x-ray source 11 and the light receiving slit 14.

The x-ray source 11 has a target placed on its focal axis I and serves to emit a beam therefrom with height h and width w, adapted to irradiate the surface Ss of the sample S through the first Soller slits 12 and the divergence slit 13. The first Soller slits 12 are for limiting the divergence of the incident x-ray beam in the vertical direction. The divergence slit 13 is for determining the width of the area on the sample surface Ss to be irradiated by this incident x-ray beam (or "the irradiated width").

The sample S is supported so as to be rotatable around a rotary axis II through its center such that the incident x-ray beam 20 (or the direction of the line connecting the aforementioned center point of the sample surface Ss and the focal axis I of the x-ray source 11) and the diffracted x-ray beam 21 (or the direction of the line connecting the center point of the sample surface Ss and the light receiving slit 14) make therebetween an angle 2θ. The diffracted x-ray beam 21 is adapted to pass through the light receiving slit 14, the second Soller slits 15 and the scatter slit 16 to be measured by the counter tube 17. The light receiving slit 14 is for the purpose of determining the resolution of the diffraction lines which are obtained, and the second Soller slits 15 are for limiting the divergence of the diffracted x-ray beam 21 in the vertical direction.

Since the sample surface Ss is tangent to the circle (or the peripheral surface of a circular cylinder) defined by the focal axis I of the x-ray source 11, the rotary axis II of the sample S and the axis III along which the light receiving slit 14 extends, the x-ray beam emitted from the x-ray source 11 is diffracted by the sample S on its surface Ss and converges at the light receiving slit 14.

The divergence slit 13 may be either a fixed slit with a fixed aperture or a variable slit with a variable aperture. If a variable slit is used as the divergence slit 13, its aperture can be varied automatically according to the angle of diffraction such that the width on the sample surface Ss irradiated by the x-ray beam can be kept constant.

The x-ray diffraction apparatus uses the counter tube 17 to obtain intensity data of diffracted x-ray beam while irradiating the sample S and varying the angle of diffraction by means of the optical system 10 thus structured. The measured data are caused to undergo data processing procedures of known kinds such as smoothing, peak search, background elimination and $K_{\alpha 2}$ elimination. A qualitative analysis is carried out by thereafter comparing these processed data with reference data on standard materials in terms of the surface spacing d and the x-ray intensity ratio $I/I_0$ where I is the peak intensity and $I_0$ is the strongest peak intensity of the measured x-rays for carrying out qualitative analysis. The x-ray diffraction apparatus and method according to this invention are characterized wherein corrections are made on the difference between the intensity levels of the measured and reference data caused by using different divergence slits to obtain them such that the measured and reference data can be compared with an improved accuracy.

The corrections according to this invention may be carried out in different manners, depending on the object of the corrections and the types of the slits. Depending on the object of corrections, the corrections may be made on the measured data, the reference data or both. Depending on the types of the slits, the corrections may be made by comparing measured data obtained with a variable slit and reference data obtained with a fixed slit, by comparing measured data obtained with a fixed slit and reference data obtained with a variable slit, by comparing measured data obtained with a variable slit and reference data obtained with another variable slit, and by comparing measured data obtained with a fixed slit and reference data obtained with another fixed slit.

Figure 3:
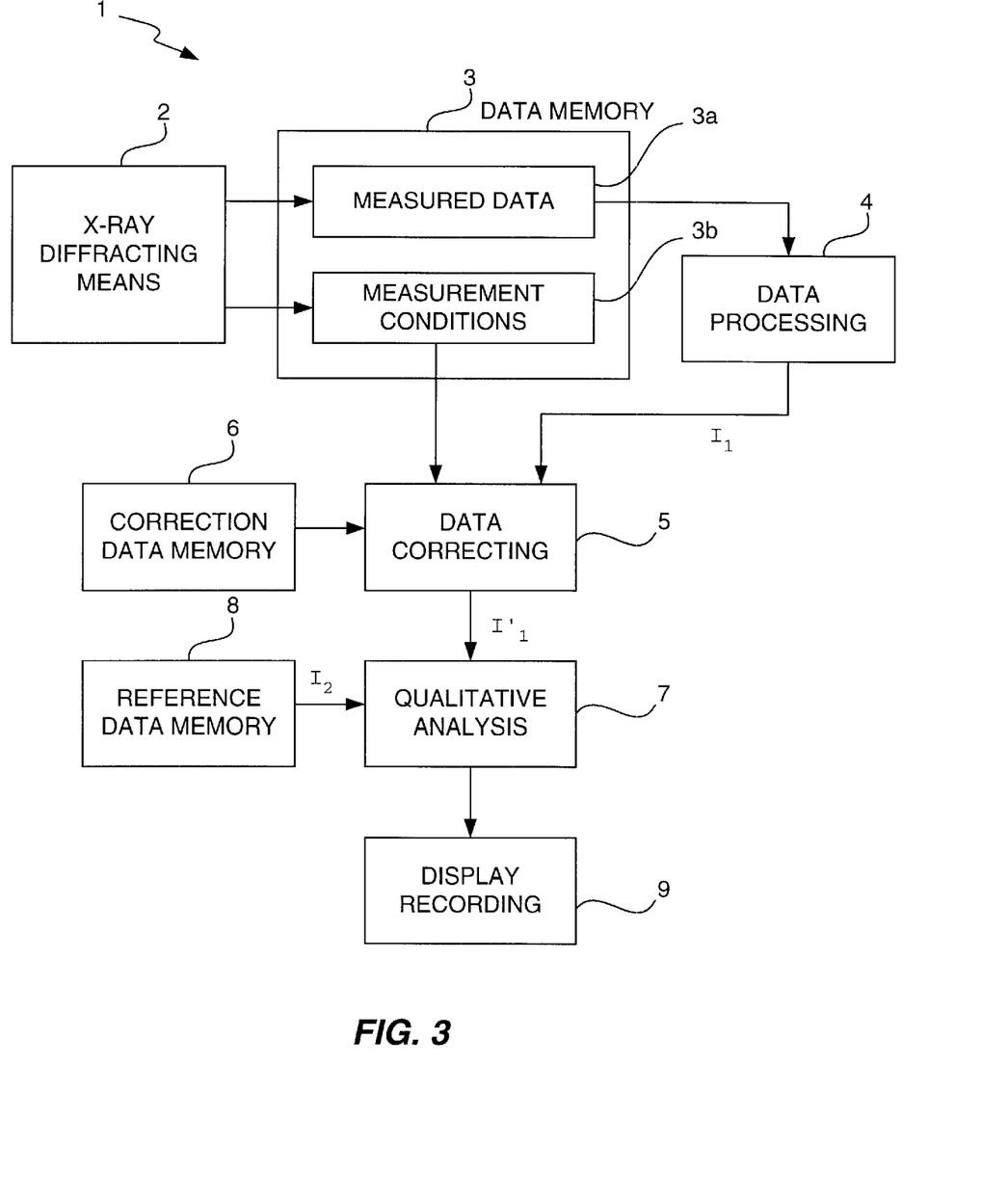
FIG. 3 is a schematic block diagram of an x-ray diffraction apparatus according to a first embodiment of the invention.

FIG. 3 shows an example of data processing according to this invention by correcting measured data and matching the intensity levels of the corrected measured data to the intensity levels of reference data. The apparatus comprises an x-ray diffracting means 2, data memory means 3, data processing means 4, data correcting means 5, correction data memory means 6, means for qualitative analysis 7 and display-recording means 9. The x-ray diffracting means 2 includes the aforementioned optical system 10 and serves to measure the intensity of diffracted x-rays at various angles of diffraction. The data memory means 3 is for storing measured data 3a thus obtained as well as conditions of measurement 3b at the time of measurement. The measured data 3a are intensity data of the diffracted x-rays and the conditions of measurement 3b include the radius R of the goniometer, the angle of divergence β in the case of a fixed slit and a selected width 2A of the area on the sample S to be irradiated ("the irradiated width") in the case of a variable slit. The data processing means 4 are for carrying out data processing on the measured data 3a such as smoothing, peak search, background elimination and $K_{\alpha 2}$ elimination to calculate the measured intensity $I_1$ of the diffracted x-rays.

The data correcting means 5 is for making corrections on the measured intensity $I_1$ thus calculated by using correction data (which may include both numerical data and formulas) stored in the correction data memory means 6 and thereby matching the intensity level of the measured data with that of the reference data. The means for qualitative analysis 7 is for carrying out a qualitative analysis by using the corrected intensity $I_1'$ calculated by the data correcting means 5 and reference data $I_2$ stored in a reference data memory means 8 and causing the result of analysis to be outputted to the display-recording means 9.

Figure 4:
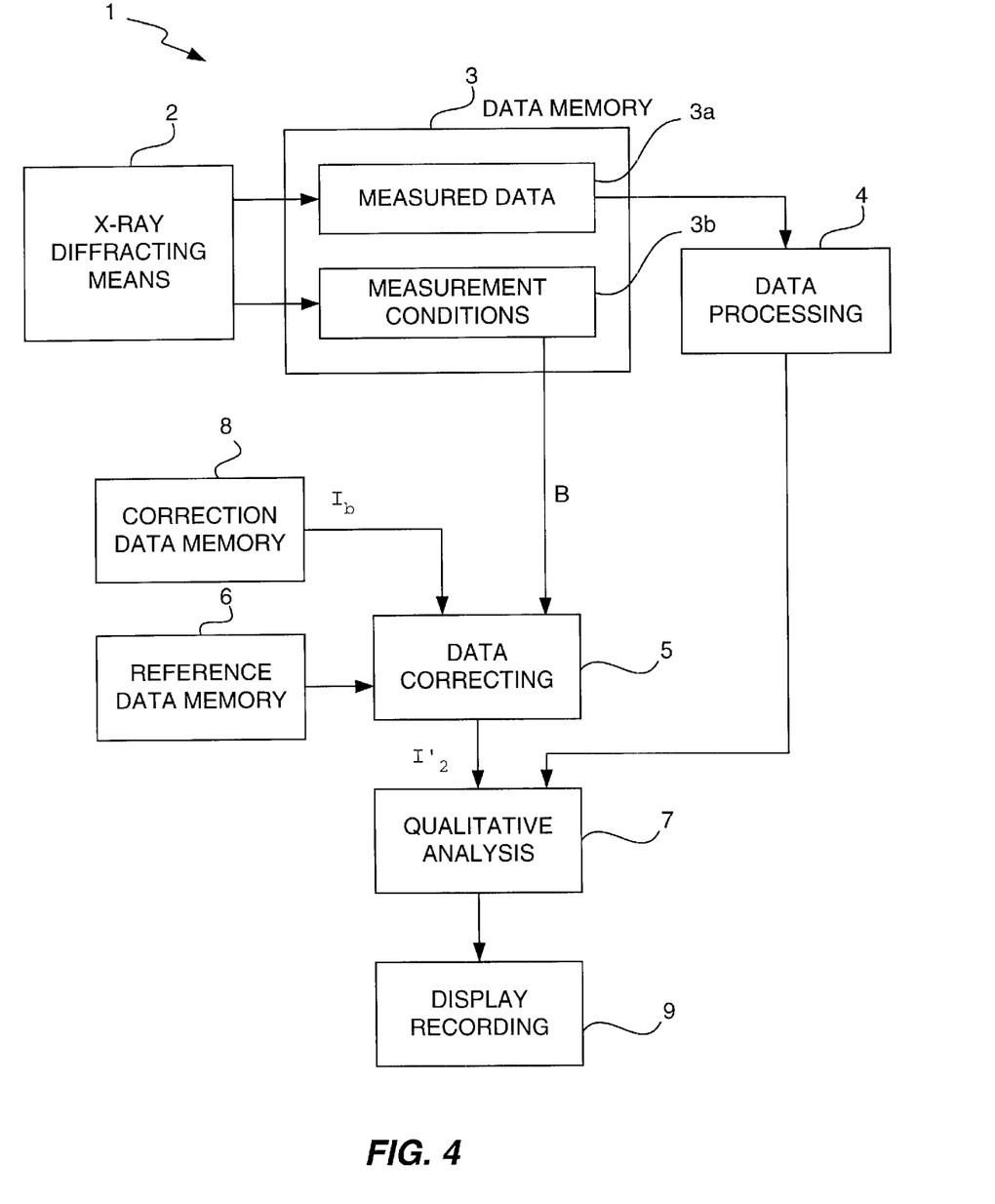
FIG. 4 is a schematic block diagram of another x-ray diffraction apparatus according to a second embodiment of the invention.

FIG. 4 shows another example of data processing by correcting reference data and matching the corrected reference data to the intensity level of measured data. It is similar to the example described above with reference to FIG. 3 except that the data correcting means 5 of FIG. 4 corrects the reference data $I_2$ by using the correction data from the correction data memory means 6 and the means for qualitative analysis 7 of FIG. 4 carries out a qualitative analysis by comparing the measured x-ray intensity $I_1$ calculated by the data processing means 4 and the corrected reference intensity $I_2'$ of diffracted x-rays obtained by the data correcting means 5.

For the sake of clarity, the divergence slit (shown at 13 in FIGS. 1 and 2) actually used for the measurement of x-ray diffraction from the sample S and the divergence slit which was used for obtaining the reference data (stored in the reference data memory means 8 shown in FIGS. 3 and 4) may be herein respectively referred to as the measured-data-obtaining divergence slit and the reference-data-obtaining divergence slit, whether their apertures are fixed or variable, in order to distinguish them one from the other. For the sake of convenience, furthermore, the means including both the optical system and the data processing means 4 for carrying out measurements on x-rays diffracted from the sample and providing the aforementioned measured data may be herein summarily referred to as the measuring means.

Both of the examples shown in FIGS. 3 and 4 may be used for comparing measured data obtained with a variable slit and reference data obtained with a fixed slit, for comparing measured data obtained with a fixed slit and reference data obtained with a variable slit, for comparing measured data obtained with a variable slit and reference data obtained with another variable slit, and for comparing measured data obtained with a fixed slit and reference data obtained with another fixed slit.

Figure 5:
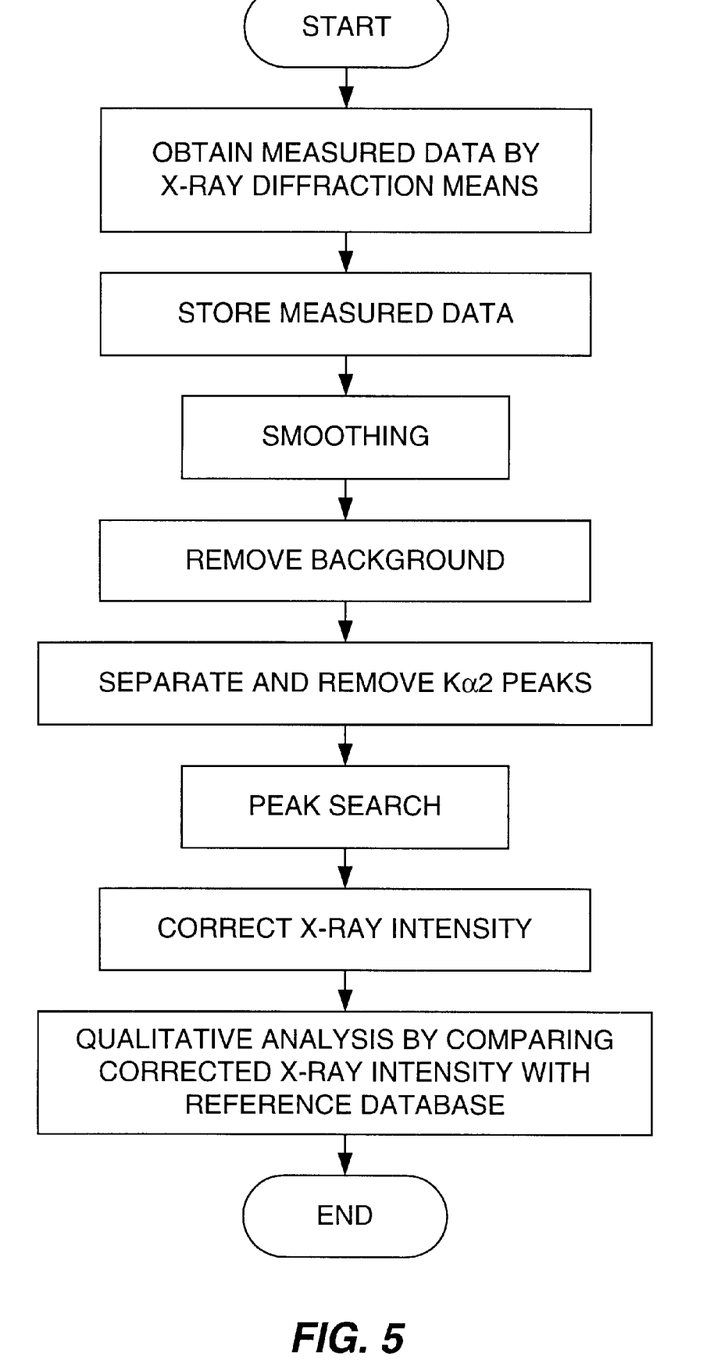
FIG. 5 is a flow chart for the operation of an x-ray diffraction apparatus of this invention.
Figure 6A:
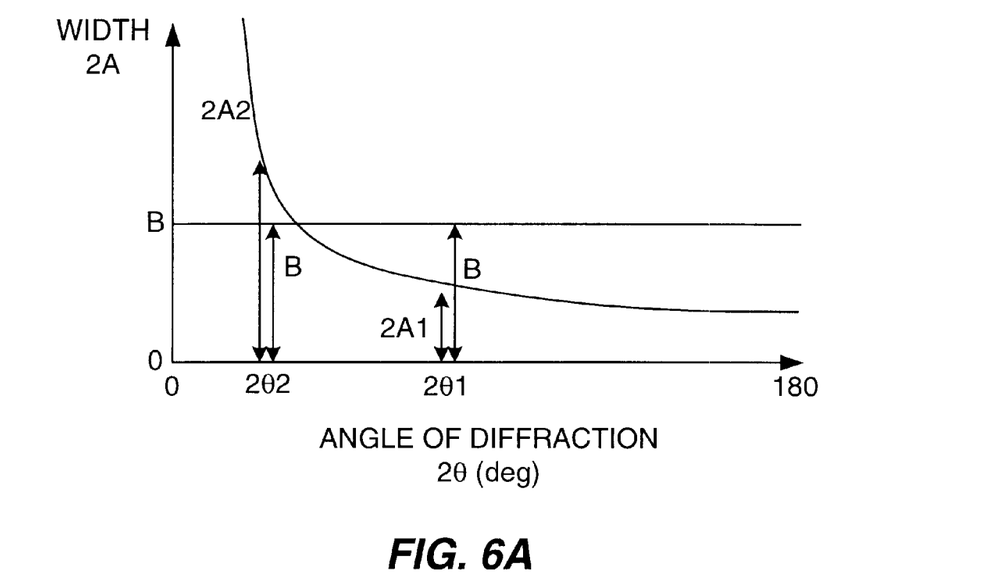
FIGS. 6A and 6B are graphs showing the functional relationships of widths of irradiated area according to the prior art with angle of diffraction.
Figure 6B:
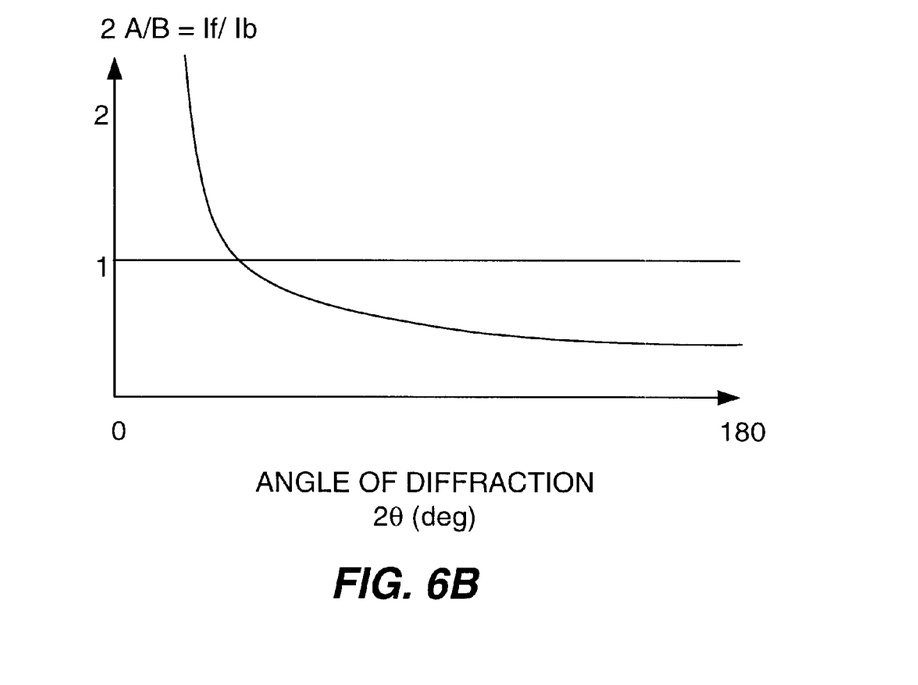

Next, FIGS. 5 and 6 will be referenced to explain a method of comparing measured data obtained by using a variable slit with reference data obtained with a fixed slit by means of the first of the examples described above by way of the data processing method according to the first of the examples described above.

To start with, measured data are obtained by means of the x-ray diffraction means 2. In this measurement, a variable slit is used as the divergence slit, and a scan is carried out to measure the intensity of the diffracted x-rays by varying the angle of diffraction $2\theta$ while controlling such that the area on the sample surface Ss irradiated by the x-rays will always have a constant width B (Step S1). The measured values of the intensity of the diffracted x-rays are saved as measured data 3a together with the corresponding angles of diffraction. The width of the irradiated area on the sample surface Ss is stored as a condition of measurement 3b (Step S2).

The data processing means 4 serves to prepare through a data processing routine the measured data to be used for the qualitative analysis. A smoothing process is carried out first by a weighted moving averaging calculation on the measured raw data to reduce the apparent statistical variations and to thereby obtain a more accurate profile (Step S3). This is done by multiplying the intensity value at each of the points of measurement by a coefficient obtained from a specified function and averaging the weighted intensity values thus obtained. Next the noise portion is eliminated by a background-removing process (Step S4) and the $K_{\alpha 2}$ peaks are separated and removed by the weighted averaging of $K_{\alpha 1}$ lines and $K_{\alpha 2}$ lines (Step S5). Peak positions are obtained thereafter as angles of diffraction from the profile thus obtained, and they are converted into a surface spacing value d. The midpoint of positions where the profile becomes zero (midpoint between bending positions) is identified as the position (Step S6). The processes in Steps S3–S6 described above are a well known data processing routine commonly carried out in x-ray diffraction analysis and hence will not be explained in detail here.

Next, the data correcting means 5 corrects the intensity $I_1$ of the diffracted x-rays at each peak position obtained b the data processing means 4 for comparing it with the reference data at a different intensity level. The intensity I of diffracted x-rays by a powder method ($I_f$ if a fixed divergence slit is used such that the irradiated width 2A varies according to the angle of diffraction, and $I_b$ if a variable divergence slit is used and the irradiation width is maintained at a constant value B) is theoretically expressed in a simple form $I=cdI_0$ where $I_0$ is the intensity of the incident x-rays, d is the irradiation width (2A or B if the measured-data-obtaining divergent slit is fixed or variable, respectively) and c is a factor which is dependent upon the so-called Lorentz polarization factor, the absorption factor related to the absorption of the incident x-rays within the sample, the temperature factor related to the reduction in the diffracted x-ray intensity due to thermal vibrations, the surface multiplicity to which the intensity of the diffracted x-rays is proportional and the crystalline structure factor, but independent of the irradiated width d. Thus, the factor c is the same for $I_f$ and $I_b$ and the ratio $I_f/I_b$ turns out to be independent of c, being equal to the ratio between the irradiated width 2A which varies with the angle of diffraction and B which is a constant), or $$I_f/I_b=2A/B=R\sin(\beta/2)\{1/\sin(\theta+\beta/2)+1/\sin(\theta-/2)\}/B$$

where $2\theta$ is the angle of diffraction and 13 is the divergence angle of the fixed slit.

FIG. 6A shows the relationship between the widths B and 2A. The width of the irradiated area is $2A_1$ corresponding to the angle of diffraction of $2\theta_1$ if a fixed slit is used but it is of the constant value B independent of the angle of diffraction if a variable slit is used. At angle of diffraction $2\theta_2$, the irradiated width is $2A_2$ by the fixed slit while it is still B by the variable slit. FIG. 6B shows the relationship between the ratio 2A/B and the angle of diffraction. The ratio 2A/B is also the ratio between the diffracted x-ray intensities when the fixed slit is used and when the variable slit is used for obtaining the measured data. Thus, if the intensity value obtained with the variable slit is multiplied by this ratio, it can be matched to the intensity level of the diffracted x-rays when the fixed slit is used. An intensity pattern of diffracted x-rays with the same intensity level is thus obtained (Step S7). Thereafter a qualitative analysis is carried out by comparing the intensity pattern corrected in Step S7 with the reference data (Step S8).

The explanation given above was by way of the data processing method according to the first of the examples described above. It goes without saying that it is also possible to correct the reference data by a method according to the second of the examples explained above by way of FIG. 4. In this case, the reference data are corrected by using B/2A as the multiplicative factor.

Although the measured data obtained by using a variable slit was compared with reference data obtained by a fixed slit in the example described above, it is similarly possible to compare measured data obtained by using a fixed slit with reference data obtained by using a variable slit. In such an application, the measured data are multiplied by 2A/B and the reference data are multiplied by B/2A for correction.

It is also possible to obtain both the measured data and the reference data from an area with a specified width or both with a fixed slit. In such applications, corrections are made respectively by using the ratio of widths $B_1/B_2$ and the ratio of the widths of the fixed slits $2A_1/2A_2$ at each of the angles θ as the multiplicative factor.

The multiplicative factor to be used for the correction need not be derived from a relationship based on a theoretical formula such as the one given above. Use may be made of an experimentally obtained correction formula or a table. It may be noted that the present invention may be used in many different ways because corrections may be made either on measured data or on reference data and the measured and reference data may be each obtained either by using a fixed slit or by using a variable slit.

In summary, the present invention makes it possible to carry out a qualitative analysis accurately because measured and reference data can be compared accurately even if the measured data on diffracted x-ray intensity and reference data are obtained under different conditions and in particular where different divergence slits are used for obtaining these data.

What is claimed is:

1. An x-ray diffraction apparatus comprising:

measuring means including an optical system with a measured-data-obtaining divergence slit for making x-rays incident on a sample through said measured-data-obtaining divergence slit, measuring intensity of diffracted x-rays by said sample, and thereby providing, as measured data, ratios between intensity values of said diffracted x-rays at different angles of diffraction;

reference data storing means for storing, as reference data, ratios between intensity values of x-rays made incidence on various reference materials through a reference-data-obtaining divergence slit and diffracted therefrom at different angles of diffraction;

data correcting means for correcting at least either of data selected from the group consisting of said measured data and said reference data so as to thereby eliminate effects of difference between x-ray intensities made incident on said sample through said measured-data-obtaining divergence slit and on said reference materials through said reference-data-obtaining divergence slit; and qualitative analysis means for carrying out qualitative analysis of said sample by comparing said measured data and said reference data after corrections are made by said data correcting means.

2. The x-ray diffraction apparatus of claim 1 wherein said measured-data-obtaining divergence slit is a fixed slit having a fixed aperture and said optical system serves to be operated such that incident x-ray intensity on said sample changes according to the angle of diffraction.

3. The x-ray diffraction apparatus of claim 1 wherein said measured-data-obtaining divergence slit is a variable slit with a variable aperture and said optical system serves to be operated by varying the aperture of said measured-data-obtaining divergence slit such that a same area on said sample is irradiated by the incident x-rays independent of angle of incidence.

4. The x-ray diffraction apparatus of claim 2 wherein said reference-data-obtaining divergence slit is a variable slit with a variable aperture, said reference data having been obtained by varying the aperture of said reference-data-obtaining divergence slit so as to have a same area on said reference materials irradiated.

5. The x-ray diffraction apparatus of claim 3 wherein said reference-data-obtaining divergence slit is a fixed slit with a fixed aperture.

6. The x-ray diffraction apparatus of claim 4 wherein said data correcting means serves to make corrections at least on said measured data.

7. The x-ray diffraction apparatus of claim 5 wherein said data correcting means serves to make corrections at least on said measured data.

8. The x-ray diffraction apparatus of claim 4 wherein said data correcting means serves to make corrections at least on said reference data.

9. The x-ray diffraction apparatus of claim 5 wherein said data correcting means serves to make corrections at least on said reference data.

10. A method of qualitative analysis comprising the steps of:

obtaining measured data by making x-rays incident on a sample through a measured-data-obtaining divergence slit, measuring intensity of diffracted x-rays by said sample, and calculating ratios between intensity values of said diffracted x-rays at different angles of diffraction;

providing, as reference data, ratios between intensity values of x-rays made incidence on various reference materials through a reference-data-obtaining divergence slit and diffracted therefrom at different angles of diffraction;

making corrections on at least either of data selected from the group consisting of said measured data and said reference data and thereby eliminating effects of difference between x-ray intensities made incident on said sample through said measured-data-obtaining divergence slit and on said reference materials through said reference-data-obtaining divergence slit; and carrying out a qualitative analysis of said sample by comparing said measured data and said reference data after said corrections are made.

11. The method of claim 10 wherein said measured-data-obtaining divergence slit is a fixed slit having a fixed aperture and incident x-ray intensity on said sample changes according to the angle of diffraction.

12. The method of claim 10 wherein said measured-data-obtaining divergence slit is a variable slit with a variable aperture, the aperture of said measured-data-obtaining divergence slit being varied such that a same area on said sample is irradiated by the incident x-rays independent of angle of incidence.

13. The method of claim 11 wherein said reference-data-obtaining divergence slit is a variable slit with a variable aperture, said reference data having been obtained by varying the aperture of said reference-data-obtaining divergence slit so as to have a same area on said reference materials irradiated.

14. The method of claim 12 wherein said reference-data-obtaining divergence slit is a fixed slit with a fixed aperture.

15. The method of claim 13 wherein said corrections are made at least on said measured data.

16. The method of claim 14 wherein said corrections are made at least on said measured data.

17. The method of claim 13 wherein said corrections are made at least on said reference data.

18. The method of claim 14 wherein said corrections are made at least on said reference data.

* * * * *